US008246638B2

United States Patent
Perez-Cruet et al.

(10) Patent No.: US 8,246,638 B2
(45) Date of Patent: Aug. 21, 2012

(54) AXIAL NEEDLE AND SUTURE DELIVERY DEVICE AND METHOD

(75) Inventors: Miguelangelo J. Perez-Cruet, Bloomfield, MI (US); John R. Pepper, Cheshire, CT (US)

(73) Assignee: MI4SPINE, LLC, Bloomfield Hills, MI (US)

( * ) Notice: Subject to any disclaimer, the term of this patent is extended or adjusted under 35 U.S.C. 154(b) by 429 days.

(21) Appl. No.: 12/497,347

(22) Filed: Jul. 2, 2009

(65) Prior Publication Data
US 2011/0004226 A1 Jan. 6, 2011

(51) Int. Cl.
*A61B 17/04* (2006.01)
(52) U.S. Cl. ........................................................ 606/145
(58) Field of Classification Search .......... 606/103–104, 606/139, 144–145, 148, 167, 181; 604/46, 604/264, 272, 411
See application file for complete search history.

(56) References Cited

U.S. PATENT DOCUMENTS

| | | | | |
|---|---|---|---|---|
| 3,946,740 A * | 3/1976 | Bassett | | 606/145 |
| 5,387,221 A * | 2/1995 | Bisgaard | | 606/148 |
| 5,499,990 A * | 3/1996 | Schulken et al. | | 606/144 |
| 5,665,096 A * | 9/1997 | Yoon | | 606/139 |
| 5,713,910 A * | 2/1998 | Gordon et al. | | 606/144 |
| 5,741,276 A * | 4/1998 | Poloyko et al. | | 606/144 |
| 6,074,404 A * | 6/2000 | Stalker et al. | | 606/144 |
| 6,454,778 B2 * | 9/2002 | Kortenbach | | 606/144 |
| 6,766,186 B1 * | 7/2004 | Hoyns et al. | | 600/431 |
| 7,381,212 B2 * | 6/2008 | Topper et al. | | 606/223 |
| 7,572,265 B2 * | 8/2009 | Stone et al. | | 606/139 |
| 2004/0034372 A1* | 2/2004 | Chu | | 606/148 |
| 2004/0249394 A1* | 12/2004 | Morris et al. | | 606/144 |
| 2004/0260314 A1* | 12/2004 | Lizardi et al. | | 606/144 |

* cited by examiner

*Primary Examiner* — Melanie Tyson
*Assistant Examiner* — Son Dang
(74) *Attorney, Agent, or Firm* — John A. Miller; Miller IP Group, PLC

(57) ABSTRACT

A needle delivery device that has particular application for providing needles for minimally invasive spinal surgical procedures. The device includes an elongated pincher having opposing rails that is slidable within a channel defined in an extended base portion. Widened end portions of the rails hold the needle and push it out of an end of the device where it is released. The pincher is then retracted to a location where the end portions can pick up a next needle to be delivered.

16 Claims, 4 Drawing Sheets

AXIAL NEEDLE AND SUTURE DELIVERY DEVICE AND METHOD

BACKGROUND OF THE INVENTION

1. Field of the Invention

This invention relates generally to a surgical device for effectively delivering a suture needle and, more particularly, to a surgical device for effectively delivering a suture needle through a tubular retractor during a minimally invasive spinal surgical procedure to repair a dural tear.

2. Discussion of the Related Art

In an attempt to preserve normal anatomical structures during spine surgery, minimally invasive surgical procedures have been devised. One such procedure involves the use of a series of muscle dilators that separate the muscle fibers of the spine to create a pathway to the spine. A Kirschner (K-wire) is initially introduced through a small incision and directed towards the spinal pathology. The position of the K-wire is visualized by a fluoroscopic imaging system to identify its location. An initial narrow diameter muscle dilator is passed over the K-wire, and the K-wire is removed and subsequent larger muscle dilators are continually passed. When the opening is large enough, an access tube or retractor is positioned around the last muscle dilator through which the surgery is performed. The inner sequential muscle dilators are then removed allowing the surgeon to operate through the tubular retractor. The retractors come in a variety of lengths and diameters for different patients and procedures.

The spinal cord and spinal nerves are covered by a watertight sac of tissue, referred to as the dura. The dura is sometimes injured during spinal surgical procedures, typically referred to a dural tear. A dural tear should be surgically repaired during the surgical procedure to prevent spinal fluid from leaking out of the sac. Because the tubular retractor through which the surgeon is performing the surgical procedure is quite narrow, the ability to perform a delicate suturing process to repair the tear is difficult. Currently no device exists that allows a surgeon to suture a dural tear easily and effectively.

SUMMARY OF THE INVENTION

In accordance with the teachings of the present invention, a suture needle delivery device is disclosed that has particular application for providing needles for minimally invasive spinal surgical procedures. The device includes an elongated pincher having opposing rails that is slidable within a channel defined in an extended base portion. Widened end portions of the rails hold the needle and push it out of an end of the device where it is released. The pincher is then retracted to a location where the end portions can pick up a next needle to be delivered.

Additional features of the present invention will become apparent from the following description and appended claims, taken in conjunction with the accompanying drawings.

DETAILED DESCRIPTION OF THE EMBODIMENTS

The following discussion of the embodiments of the invention directed to a suture needle delivery device is merely exemplary in nature, and is in no way intended to limit the invention or its applications or uses. For example, the suture needle delivery device of the present invention has particular application for suturing the dura in a minimally invasive spinal surgery procedure. However, as will be appreciated by those skilled in the art, the suture delivery device of the invention may have application for other surgical and non-surgical procedures.

Figure 1:
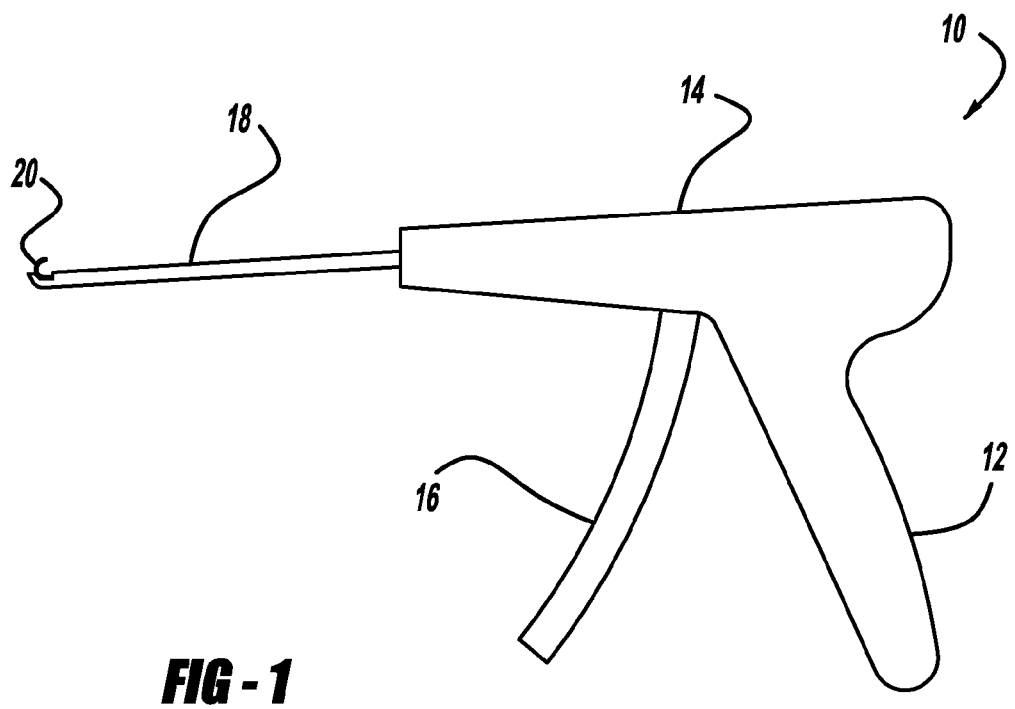
FIG. 1 is a side view of a suture needle delivery device.

FIG. 1 is a side view of a suture needle delivery device 10 that effectively delivers a needle or suture to a surgeon who is suturing a wound during a surgical procedure. The device has particular application for delivering a suture needle to the proper location for a surgeon using a minimally invasive surgical tubular retractor during spinal surgery for suturing the dura to repair a dural tear.

The device 10 includes a handle 12 attached to a body 14 and a trigger 16 extending from the body 14 adjacent to the handle 12. A needle delivery assembly 18 is attached to and extends from the body 14 and includes most of the operative features of the device 10, as will be discussed in detail below. The surgeon will squeeze the trigger 16 during the surgical procedure which will cause the device 10 to advance and deliver a needle 20 to the location that requires suturing, where it is released from the device 10. The surgeon can then grasp the needle 20 with a suitable instrument to place it at the proper location. The needle 20 can be made of any suitable material, such as a deformable element, for example, titanium, or a shape memory alloy, for example, nitanol.

Figure 2:
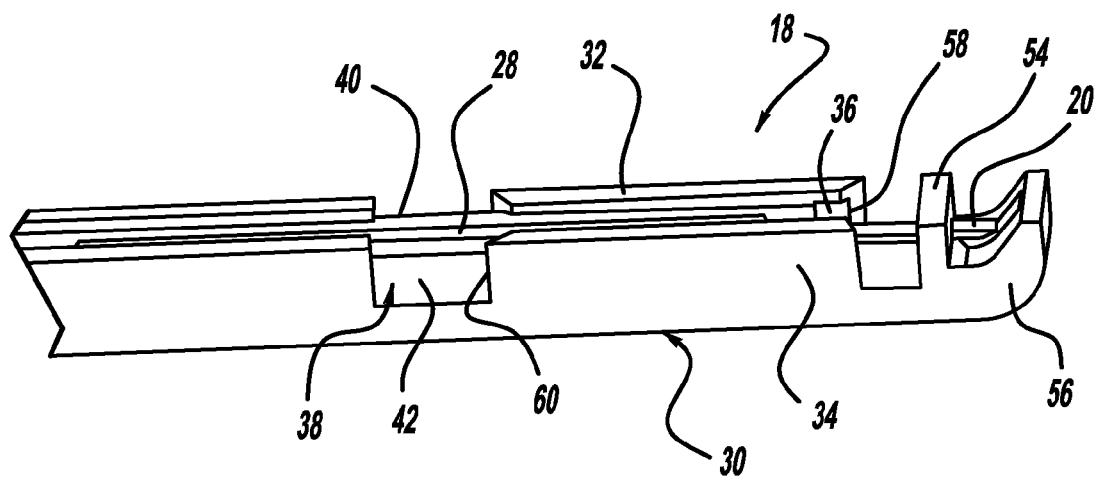
FIG. 2 is a cut-away, perspective view of a delivery end of the suture needle delivery device shown in FIG. 1.
Figure 3:
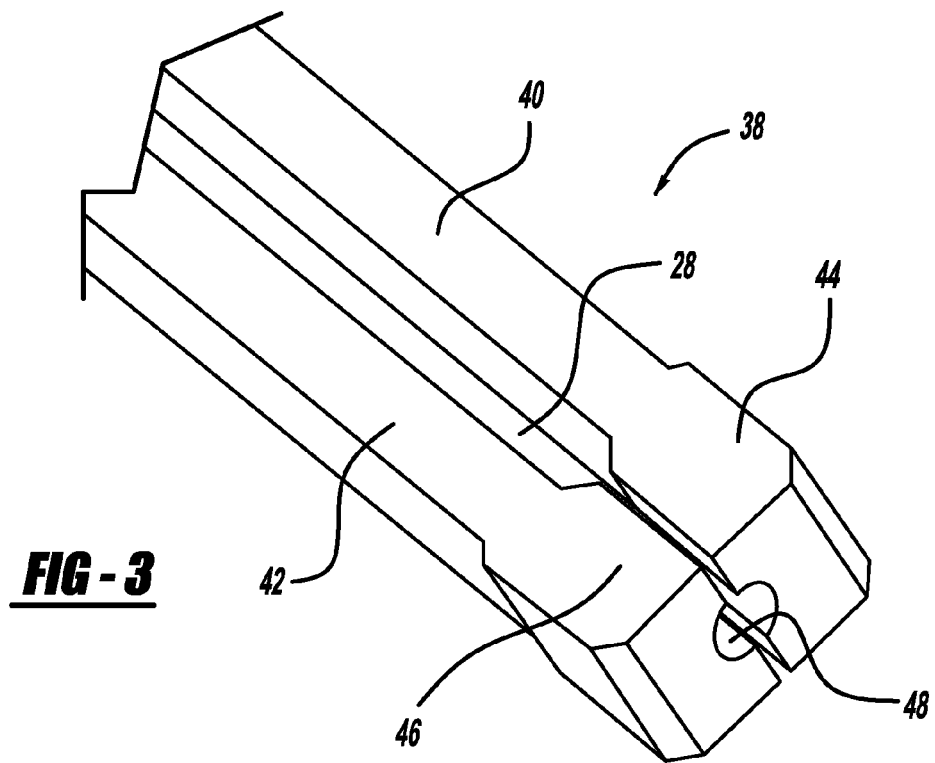
FIG. 3 is a cut-away, perspective view of an end portion of a pincher used in the suture needle delivery device shown in FIG. 1.

FIG. 2 is a cut-away, perspective view of the needle delivery assembly 18 including a specially configured base portion 30 having side walls 32 and 34 defining a channel 36 therebetween. An elongated pincher 38 including opposing rails 40 and 42 defining a slot 28 therebetween is positioned and slidable within the channel 36 in the base portion 30 where a top edge of the walls 32 and 34 hold the pincher 38 within the channel 36, as shown. FIG. 3 is a cut-away, perspective view of the pincher 38 showing the rails 40 and 42 having widened end portions 44 and 46, respectively, defining a circular opening 48. When the pincher 38 is positioned within the channel 36, the space between the walls 32 and 34 is selected so that the end portions 44 and 46 are pushed together with a spring action provided by the slot 28 so that the diameter of the opening 48 holds the needle 20.

Figure 4:
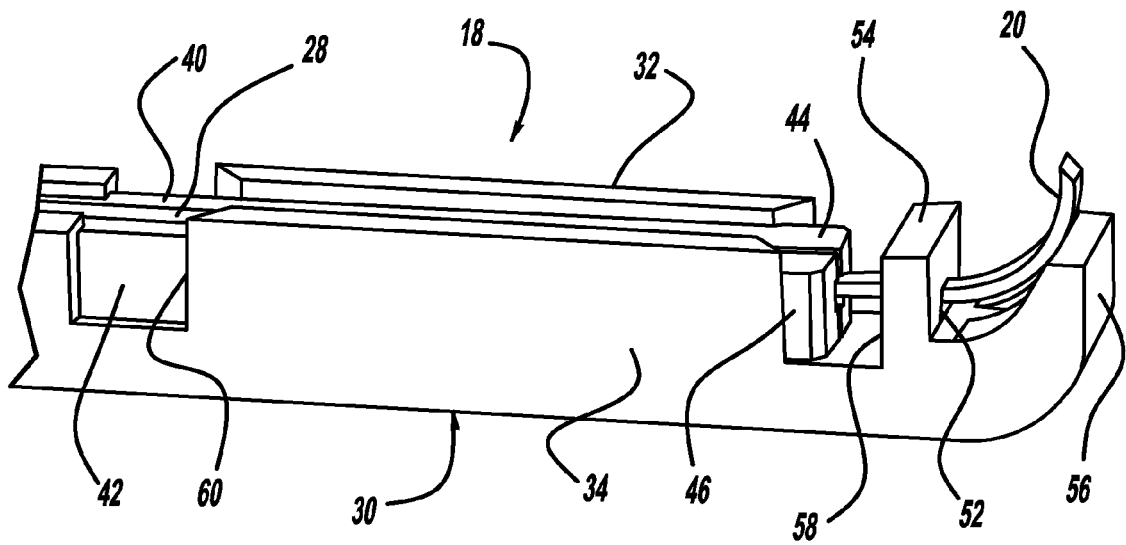
FIG. 4 is a cut-away, perspective view of a delivery end of the suture needle delivery device shown in FIG. 1 with a suture needle partially extended.
Figure 5:
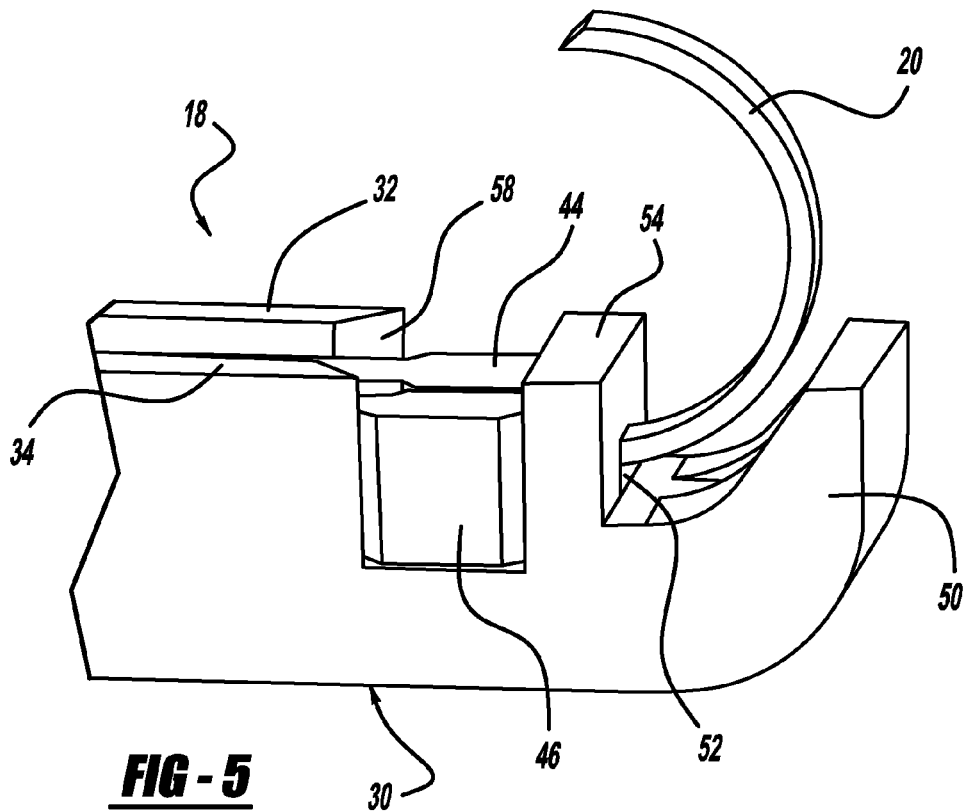
FIG. 5 is a cut-away, perspective view of a delivery end of the suture and needle delivery device shown in FIG. 1 with a suture needle fully extended.
Figure 6:
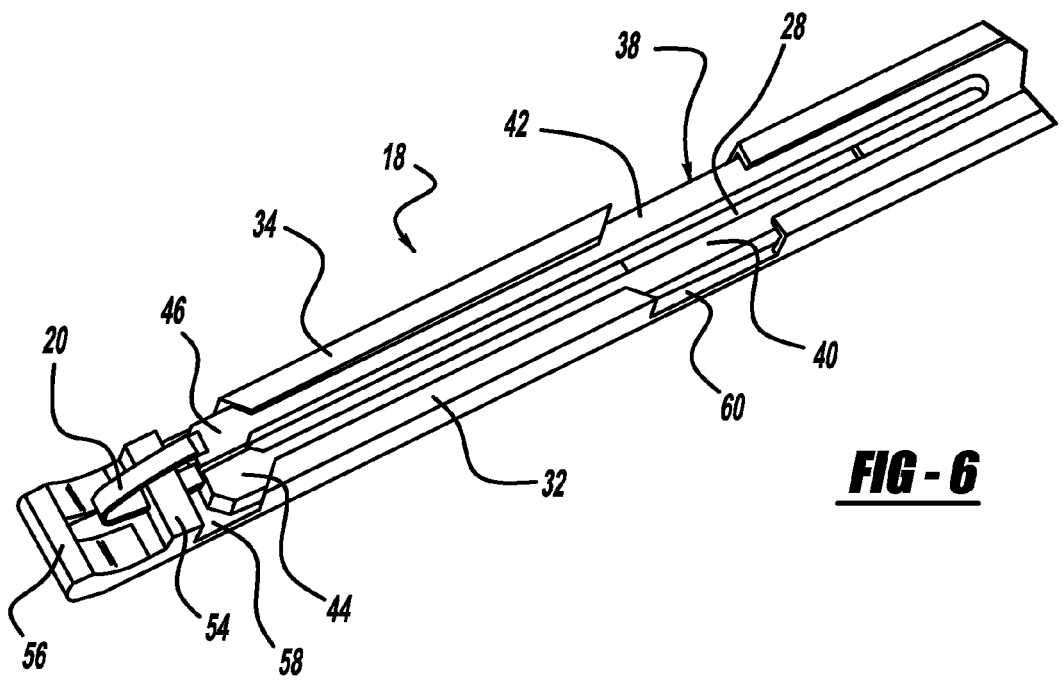
FIG. 6 is a top cut-away, top perspective view of a delivery end of the suture and needle delivery device shown in FIG. 1 with a suture needle fully extended.

Pulling the trigger 16 towards the handle 12 causes the pincher 38 to be advanced through the channel 36 by any suitable manner, such as by a pushing member (not shown), which causes the needle 20 extending therefrom to be pushed through an opening 52 in a barrier 54 formed in the base portion 30, as shown. As the needle 20 continues to advance, it is pushed against a curved end barrier 56, which causes the needle 20 to bend upward allowing it to be grasped by the surgeon to be placed through the tissue being sutured. FIGS. 4, 5 and 6 show detailed views of the end of the delivery assembly 18 where the needle 20 is being extended from the device 10.

When the end portions 44 and 46 reach an opening 58 between an end of the walls 32 and 34 and the barrier 54 they will slide apart under the spring action provided by the slot 28, which increases the diameter of the opening 48 and releases the needle 20 so that the surgeon can remove the needle 20 from the device 10. If the needle 20 is made of shape memory alloy, and is held in a straight configuration where its memory shape is curved, it will readily return to the curved shape when it is released from the pincher 38.

Figure 7:
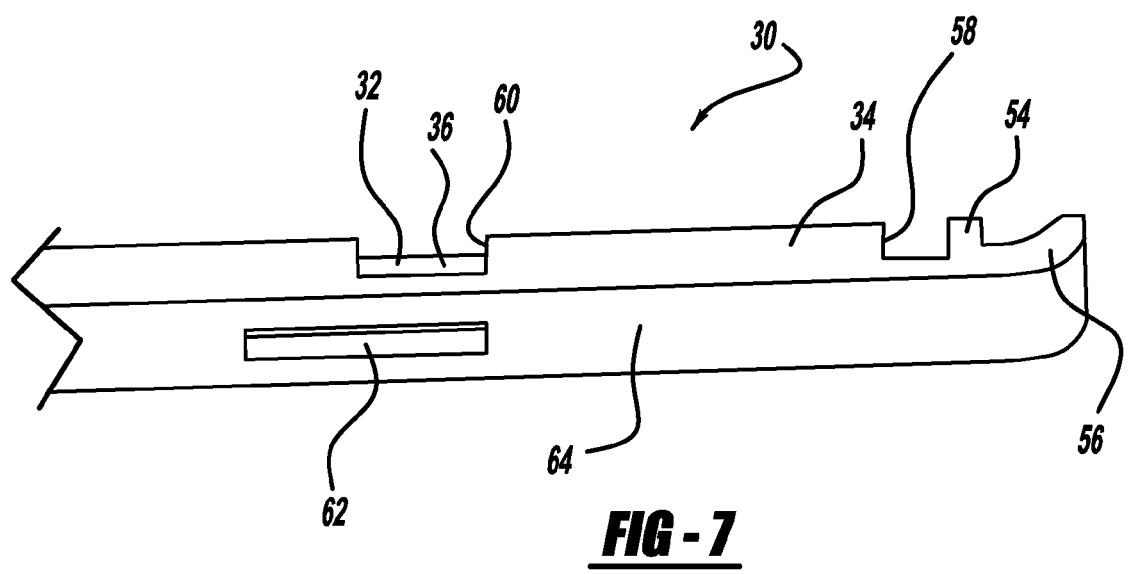
FIG. 7 is a cut-away, bottom perspective view of a delivery end of the suture needle delivery device shown in FIG. 1 showing a slot for loading suture needles into the device.

Releasing the trigger 16 causes the pincher 38 to retract back to an original location where it can be loaded with another needle to allow the surgeon to continue with the suturing operation. Particularly, the pincher 38 slides back in the channel 36 to a location where the end portions 44 and 46 are positioned within an opening 60 in the walls 32 and 34 that allows the end portions 44 and 46 to slide apart under the spring action provided by the slot 28 so that the opening 48 is again increased. Another needle can be loaded into the pincher 38 between the rails 40 and 42 into the opening 48 through a slot 62 in a bottom plate 64 of the base portion 30 so that when the trigger 16 is pulled again and the pincher 38 is advanced, the pincher 38 grabs the new needle by the closing of the opening 48 and extends it in the manner discussed above. FIG. 7 is a bottom view of the base portion 30 showing the slot 28.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A needle delivery device comprising:
   a body;
   a handle coupled to the body;
   a trigger coupled to the body; and
   a delivery assembly extending from the body, said delivery assembly including an elongated base member including side walls defining a channel therebetween and an elongated pincher including opposing rails where each rail has a widened end portion, said delivery assembly further including an end member and a first opening between an end of the side walls and the end member, wherein a needle is grasp by the widened portions of the rails and is advanced by the pincher until the widened end portions are positioned within the first opening and separate to release the needle.

2. The device according to claim 1 wherein the channel is configured to have a width dimension that pushes the widened end portions of the rails together under tension to hold the needle so that a bias of a slot between the rails causes the widened portions to separate when the widened portions are in the first opening.

3. The device according to claim 1 wherein the delivery assembly includes a barrier positioned between the end of the side walls and the end member, said barrier including a hole through which the needle extends, said first opening being between the end of the side walls and the barrier.

4. The device according to claim 1 wherein the handle is coupled to the body in such a manner that causes the pincher to be advanced within the channel when the trigger is pulled.

5. The device according to claim 1 wherein the delivery assembly includes a second opening in the side walls closer to the body than the first opening, said pincher being retracted in the channel to a position so that the widened portions of the rails are positioned within the second opening and separate so as to allow the needle to be inserted into the delivery assembly.

6. The device according to claim 5 wherein the base member includes a bottom plate having a loading slot that is aligned with the second opening, said needle being inserted into the delivery assembly through the loading slot.

7. The device according to claim 1 wherein the needle is made of a shape memory alloy.

8. The device according to claim 7 wherein the alloy is nitinol.

9. The device according to claim 1 wherein the end member includes an angled surface facing the first opening that causes the needle to exit the device in a curved format.

10. The device according to claim 1 wherein the side walls include a top edge that holds the pincher within the channel.

11. A needle delivery device comprising:
    a body; and
    a delivery assembly extending from the body, said delivery assembly including an elongated base member including side walls defining a channel therebetween and an elongated pincher having opposing rails, said pincher being slidably moveable within the base member and being operable to axially move a needle through the delivery assembly by grasping the needle between the opposing rails, said needle being made of a shape memory alloy that is restored to a non-linear shape when it is ejected from the delivery assembly, wherein the opposing rails of the elongated pincher each include a widened end portion and the base member includes a first opening, said needle being grasped between the widened end portions of the opposing rails, said channel being configured to have a width dimension that pushes the widened end portions of the rails together under tension to hold the needle so that a bias of a slot between the rails causes the widened portions to separate when the widened portions are in the first opening, and wherein the delivery assembly includes a second opening in the side walls closer to the body than the first opening, said pincher being retracted in the channel to a position so that the widened portions of the rails are positioned within the second opening and separate so as to allow the needle to be inserted into the delivery assembly.

12. The device according to claim 11 wherein the alloy is nitinol.

13. The device according to claim 11 wherein the base member includes an angled end barrier, said needle being axially pushed against the end barrier as it is being ejected.

14. The device according to claim 11 wherein the delivery assembly includes an end member and a barrier positioned between the end of the side walls and the end member, said barrier including a hole through which the needle extends.

15. A needle delivery device comprising:
    a body; and
    a delivery assembly extending from the body, said delivery assembly including an elongated base member having side walls defining a channel therebetween and an elongated pincher having opposing rails, said pincher being slidably moveable within the base member and being operable to axially move a needle through the delivery assembly by grasping the needle between the opposing rails, wherein the opposing rails of the elongated pincher each include a widened end portion and the base member includes a first opening, said needle being grasped between the widened end portions of the opposing rails, said channel being configured to have a width dimension that pushes the widened end portions of the rails together under tension to hold the needle so that a bias of a slot between the rails causes the widened portions to separate when the widened portions are in the first opening, and wherein the delivery assembly includes a second opening in the side walls closer to the body than the first opening, said pincher being retracted in the channel to a position so that the widened portions of the rails are positioned within the second opening and separate so as to allow the needle to be inserted into the delivery assembly.

16. The device according to claim 15 wherein the delivery assembly includes an end member and a barrier positioned between the end of the side walls and the end member, said barrier including a hole through which the needle extends.

\* \* \* \* \*